United States Patent [19]

Auffet

[11] Plant 4,914

[45] Nov. 2, 1982

[54] APPLE TREE

[76] Inventor: Johnny W. Auffet, Rte. 2, Sallisaw, Okla. 74955

[21] Appl. No.: 124,243

[22] Filed: Feb. 25, 1980

[51] Int. Cl.[3] ..... A01H 5/03

[52] U.S. Cl. ..... Plt./34

[58] Field of Search ..... Plt./34

*Primary Examiner*—Robert E. Bagwill

*Attorney, Agent, or Firm*—Head & Johnson

[57] ABSTRACT

An apple tree bearing non-russeting fruit which is firm though early, and which has a clean, clear flavor when fully ripe.

6 Drawing Figures

BACKGROUND OF THE INVENTION

The present invention relates to a new and distinct variety of apple tree, which was discovered by me and believed to be a chance seedling or mutation, which is a whole tree on my cultivated property in Sequoyah County, Okla.

At the time of the discovery I was growing an orchard of the apple variety known as "Yellow Delicious". At the time this tree was about four years old it came to my attention that it was producing apples which have some distinct and outstanding characteristics which were materially different in a number of respects from the characteristics of the "Yellow Delicious" variety, which were growing under the same conditions in the same area adjacent thereto.

Qualified experts, who have seen the new variety, have attested to the unique combination of characteristics which pass through succeeding propagations.

The accompanying photographic drawings show typical specimens of the fruit of my new variety of apple tree, as depicted in color as nearly true as is reasonably possible.

Some of the unique characteristics which are apparently established are:

(1) A smooth non-russeting skin;

(2) The fruit has a high Vitamin C, or ascorbic acid, content. Tests on fruit that had been stored for over a month indicate at least 5.45 milligrams of absorbic acid per 100 grams of apple tissue;

(3) The taste is tart like a Jonathan but has a clean clear taste of its own when fully ripe;

(4) Exceptionally firm, for an early apple, and firmer than the Yellow Delicious;

(5) Resists bruising and is essentially non-browning when bruised or cut; an exceptional fruit for drying purposes as it will not turn brown when dried or frozen. One was cut in half and left in the refrigerator for about one week, resulting only in a very faint brown tone;

(6) The tartness makes the fruit extra good for cooking purposes, as in applesauce, pies, etc.;

(7) The tree is of the spur type;

(8) The following is a detailed description of my new variety:

Locality where grown and observed: Just south of Interstate 40 and west of Fort Smith, Ark., twenty-five miles.

Date of first and last picking: First two weeks of August.

The tree: About the size of the Yellow Delicious, although I do not know the full size of the tree as it is not yet fully grown. Trunk and branches are light green coloration with smooth bark. The fruit spurs appear to have a greater number of leaves than the Yellow Delicious.

Lenticels: Fewer than on the Yellow Delicious. The color is of a yellowish-green color, lighter than the Yellow Delicious.

Leaves: Slightly wider and longer than the Yellow Delicious. The ribs or veins of the leaves are curved more outwardly than upwardly from the leaf stem, as opposed to straight outwardly and upwardly in the Yellow Delicious. The length is about five (5) inches, exclusive of the leaf stem. The width is about two and one half (2½) inches. The margin is medium to coarsely serrated.

Petiole: Slightly thicker than the Yellow Delicious (about 1¼ to 1½ inches long; slightly thicker.

Branches: Have wide angle crotches, similer to veins on the leaves.

Flowers: Similar to those of the Yellow Delicious and about the same blooming period.

Fruit:

*Ripening.*—Thirty (30) days prior to Yellow Delicious.

*Size.*—Large for an early apple. Will pack about 88 count to 113 count per bushel.

*Axial diameter.*—Averages from 2¾ to 3 inches.

*Transverse diameter.*—At largest point about the same as axial diameter.

*Shape.*—Similar to a Yellow Delicious.

*Calyx.*—Closed more than the Yellow Delicious.

*Skin.*—Smooth, very thin, and with fewer lenticels when compared to a Yellow Delicious.

*General color effect.*—Predominantly yellow with slight greenish hue and, in some instances, with a reddish blush on the shoulder. Color is similar to Western States Yellow Delicious.

*Core.*—White flesh; relatively small when compared to a Yellow Delicious. Juicy.

*Seed.*—Up to 10 per apple; average ¼ inch in length and ⅛ inch in width. Color: light to dark brown.

*Use.*—Eating; especially as an early apple with a light tartness. Good for pies and cooking purposes.

*Keeping quality.*—Apple will stay firmer and crisper longer than other apples at room temperature.

*Resistance to insects and diseases.*—Fairly resistant to fire blight; fairly resistant to scab — none noticeable; resistant to mildew.

*Key feature.*—Self-thinning characteristic of the tree — similar to a Summer Champion with very little hand or chemical thinning required. Fruit shown is six (6) weeks old. Specimens cut and open to the atmosphere resist browning, especially when refrigerated.

I claim:

1. A new and distinct variety of apple tree substantially as described and illustrated and particularly characterized by a firm, non-russeting, bruise resistant, thin-skinned, fruit, maturing about thirty (30) days prior to "Yellow Delicious" grown in the same area, and further characterized by a high ascorbic acid (Vitamin C) content, while the tree has self-thinning characteristics and the leaves have ribs or veins which curve outwardly more than upwardly.

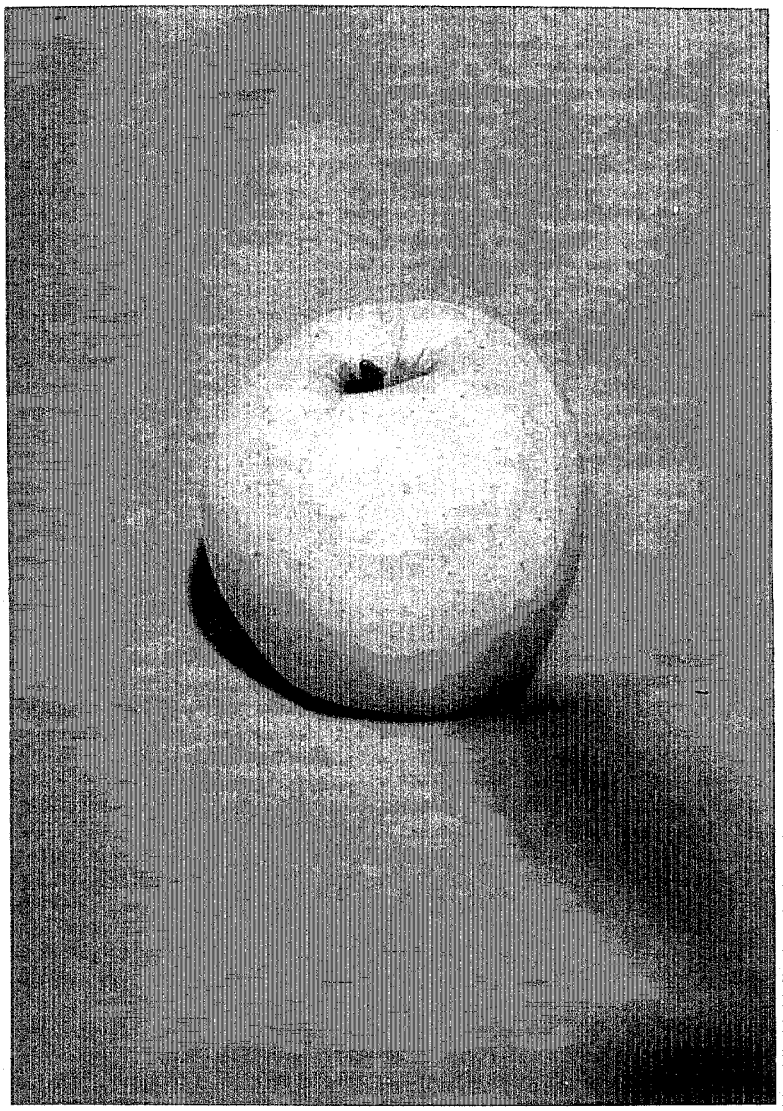

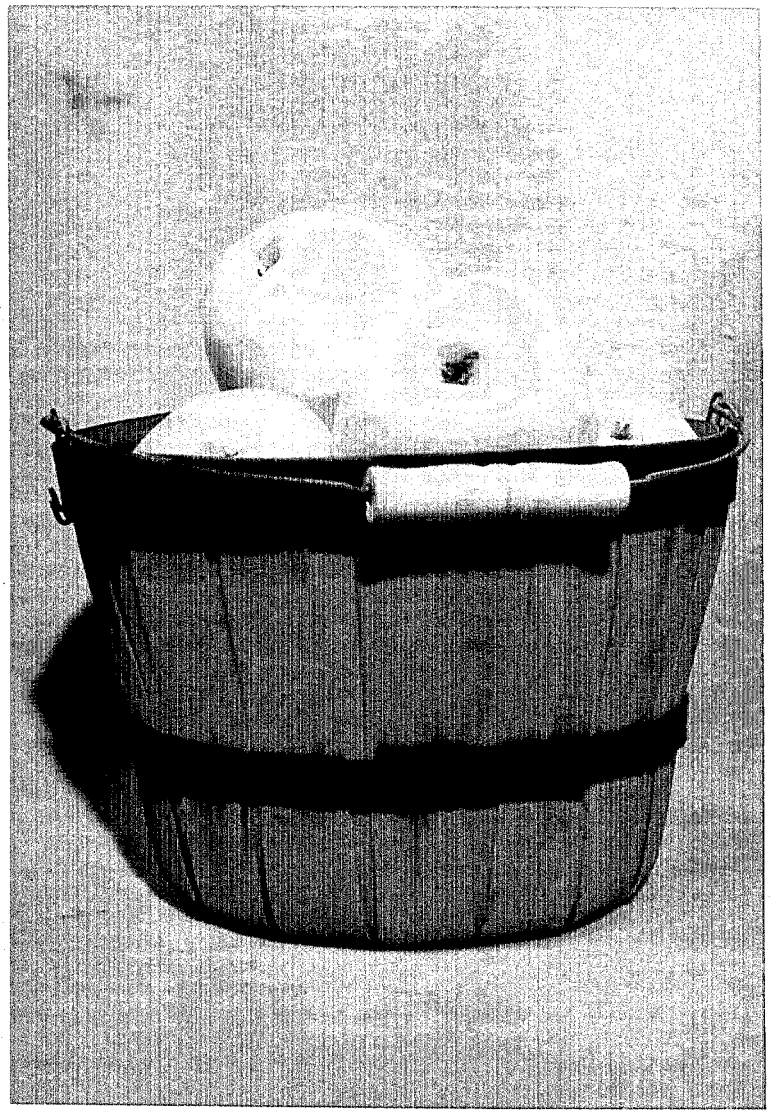

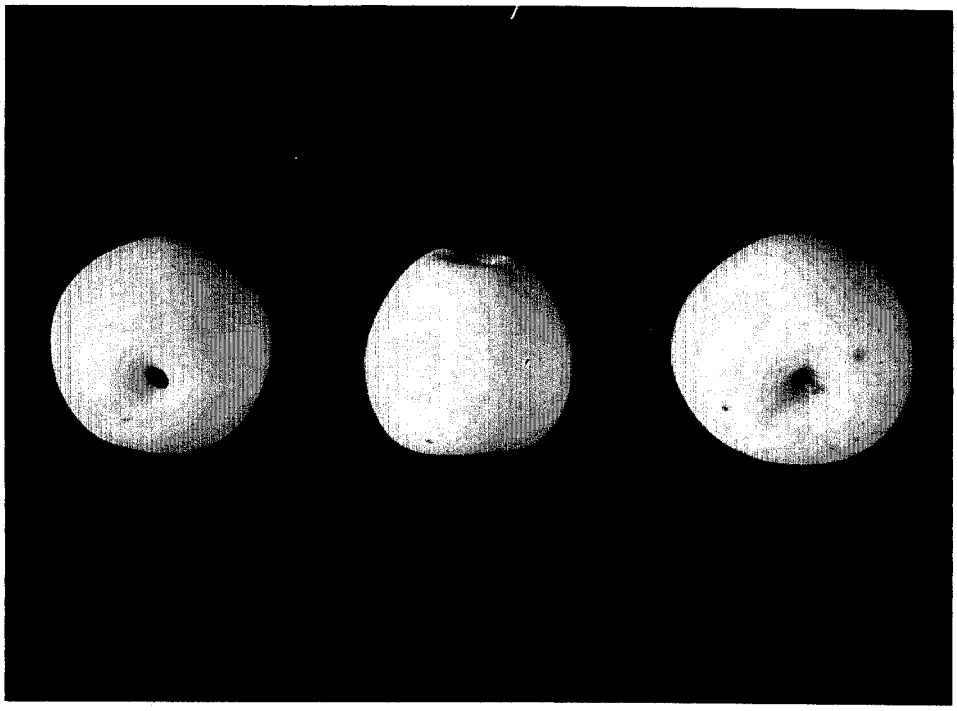

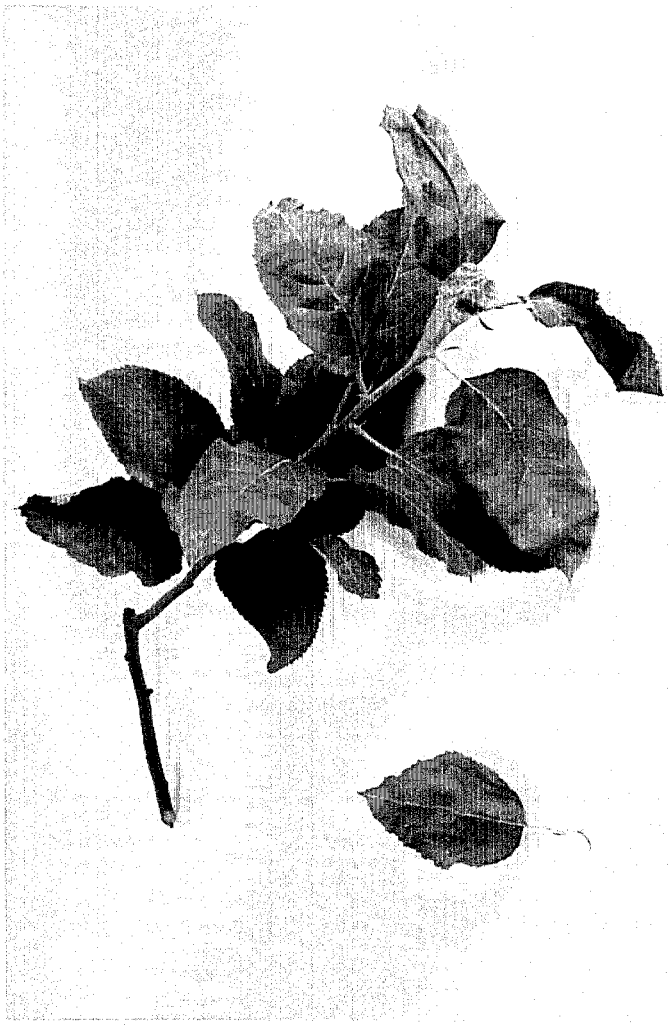

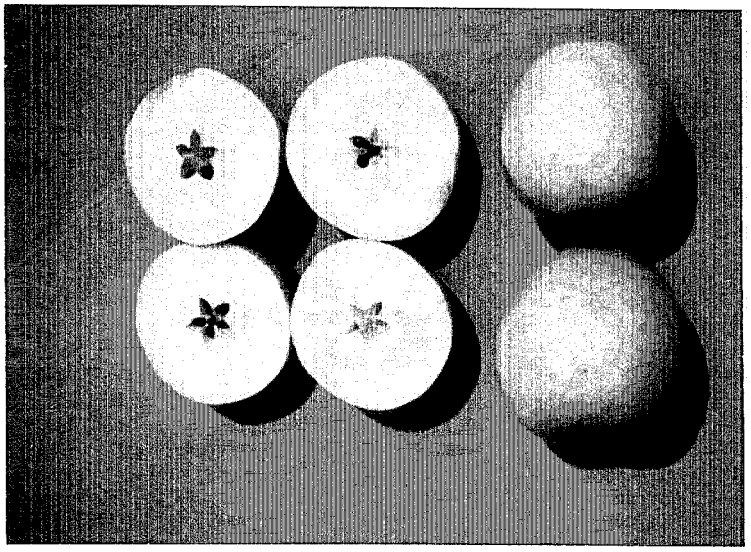
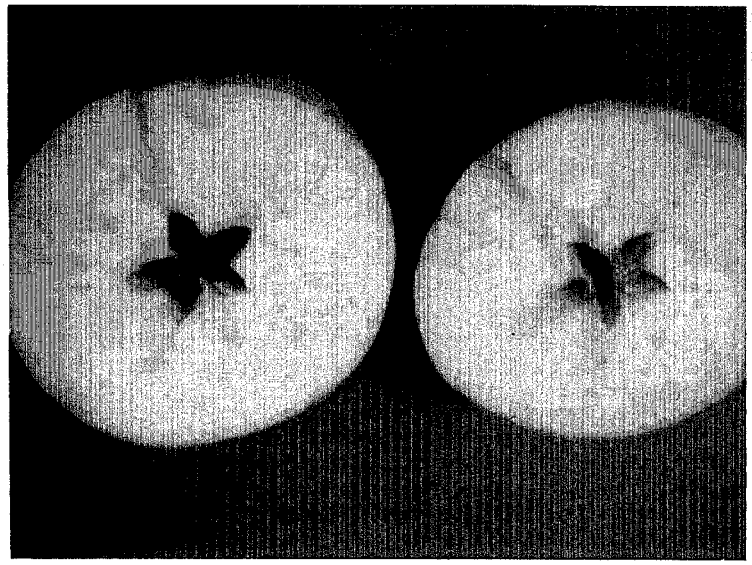

* * * * *